United States Patent
Akao

(10) Patent No.: US 11,658,500 B2
(45) Date of Patent: May 23, 2023

(54) POWER SUPPLY UNIT FOR AEROSOL INHALER

(71) Applicant: JAPAN TOBACCO INC., Tokyo (JP)

(72) Inventor: Takeshi Akao, Tokyo (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 16/745,057

(22) Filed: Jan. 16, 2020

(65) Prior Publication Data
US 2020/0229503 A1 Jul. 23, 2020

Related U.S. Application Data

(60) Provisional application No. 62/793,551, filed on Jan. 17, 2019.

(30) Foreign Application Priority Data

Feb. 28, 2019 (JP) .............................. JP2019-035974

(51) Int. Cl.
*H02J 7/00* (2006.01)
*A24F 40/90* (2020.01)
(Continued)

(52) U.S. Cl.
CPC ............ *H02J 7/0068* (2013.01); *A24F 40/40* (2020.01); *A24F 40/50* (2020.01); *A24F 40/51* (2020.01);
(Continued)

(58) Field of Classification Search
CPC .......... H02J 7/0068; H02J 7/04; H02J 7/0042; H02J 7/007194; H02J 7/0045; H02J 7/005;
(Continued)

(56) References Cited

U.S. PATENT DOCUMENTS

| 8,907,631 B1* | 12/2014 | Gurries | H02J 7/0077 320/138 |
| 2006/0238169 A1* | 10/2006 | Baker | H02J 7/0091 320/150 |

(Continued)

FOREIGN PATENT DOCUMENTS

| JP | 2007-215251 A | 8/2007 |
| JP | 2012-010525 A | 1/2012 |

(Continued)

OTHER PUBLICATIONS

Decision to Grant Patent issued in related Japanese Patent Application No. 2019-035974 dated Sep. 24, 2019.
(Continued)

*Primary Examiner* — Nathaniel R Pelton
(74) *Attorney, Agent, or Firm* — Venable LLP

(57) ABSTRACT

A power supply unit for an aerosol inhaler includes: a power supply able to discharge power to a load for generating an aerosol from an aerosol generation source; and a charger including an information input part, and configured to be able to supply one of a first charging voltage and a second charging voltage lower than the first charging voltage to the power supply, based on an input value which is input from the information input part. A fixed value which is predetermined as one input value can be input to the information input part, and the fixed value is a value for supplying the second charging voltage to the power supply.

16 Claims, 7 Drawing Sheets

(51) Int. Cl.
*A24F 40/51* (2020.01)
*A24F 40/60* (2020.01)
*A61M 15/00* (2006.01)
*H05K 1/18* (2006.01)
*A24F 40/53* (2020.01)
*A24F 40/50* (2020.01)
*H05K 1/14* (2006.01)
*A24F 40/40* (2020.01)
*G05F 3/18* (2006.01)
*H01M 10/42* (2006.01)
*A24F 40/95* (2020.01)
*H02J 7/04* (2006.01)
*H01M 10/48* (2006.01)
*A61M 15/06* (2006.01)
*A24F 40/30* (2020.01)

(52) U.S. Cl.
CPC .............. *A24F 40/53* (2020.01); *A24F 40/60* (2020.01); *A24F 40/90* (2020.01); *A24F 40/95* (2020.01); *A61M 15/009* (2013.01); *G05F 3/18* (2013.01); *H01M 10/425* (2013.01); *H01M 10/48* (2013.01); *H02J 7/005* (2020.01); *H02J 7/007* (2013.01); *H02J 7/0042* (2013.01); *H02J 7/0045* (2013.01); *H02J 7/0063* (2013.01); *H02J 7/007194* (2020.01); *H02J 7/04* (2013.01); *H05K 1/14* (2013.01); *H05K 1/181* (2013.01); *A24F 40/30* (2020.01); *A61M 15/0003* (2014.02); *A61M 15/06* (2013.01); *A61M 2205/3653* (2013.01); *A61M 2205/50* (2013.01); *A61M 2205/8206* (2013.01); *A61M 2205/8237* (2013.01); *A61M 2205/8243* (2013.01); *H05K 2201/10015* (2013.01); *H05K 2201/10022* (2013.01); *H05K 2201/10174* (2013.01)

(58) Field of Classification Search
CPC .. H02J 7/0063; H02J 7/007; H02J 7/02; H02J 7/34; H02J 1/02; H02J 7/0044; H02J 2207/10; H02J 2207/20; H02J 2207/50; H02J 7/00; H02J 7/345; H02J 7/0029; H02J 7/00309; H02J 7/007192; H02J 7/0091; A24F 40/95; A24F 40/40; A24F 40/50; A24F 40/53; A24F 40/90; A24F 40/51; A24F 40/60; A24F 40/30; A24F 40/57; A24F 40/10; A24F 47/00; H01M 10/425; H01M 10/44; H01M 10/48; H01M 10/00; G05F 3/18; H05K 1/14; H05K 1/181; H05K 2201/10022; H05K 2201/10015; H05K 2201/10174; H05K 7/1422; A61M 15/009; A61M 2205/3653; A61M 2205/8206; A61M 15/0003; A61M 15/06; A61M 2205/8243; A61M 2205/50; A61M 2205/8237; A61M 2205/3368; A61M 2205/581; A61M 2205/582; A61M 2205/3375; A61M 2205/52; A61M 2205/583; A61M 2016/0018; A61M 2016/0027; A61M 15/0021; A61M 11/042; Y02E 60/10; H02M 3/156; H02M 7/02; H02M 1/14; H02M 1/44; H02M 1/00; H02M 1/32; H02H 7/20
USPC ......................................................... 131/329
See application file for complete search history.

(56) References Cited

U.S. PATENT DOCUMENTS

| | | |
|---|---|---|
| 2007/0188135 A1 | 8/2007 | Odaohhara |
| 2009/0160405 A1 | 6/2009 | Takeda et al. |
| 2010/0079112 A1* | 4/2010 | Nagashima ........... H02J 7/0029 320/134 |
| 2013/0026997 A1 | 1/2013 | Takeda et al. |
| 2013/0113438 A1* | 5/2013 | Aradachi ............. H01M 50/213 320/162 |
| 2014/0014125 A1 | 1/2014 | Fernando et al. |
| 2014/0028267 A1 | 1/2014 | Lee |
| 2015/0020831 A1 | 1/2015 | Weigensberg et al. |
| 2015/0069952 A1 | 3/2015 | Xiang |
| 2015/0173124 A1* | 6/2015 | Qiu ......................... A24F 40/60 131/328 |
| 2016/0118840 A1 | 4/2016 | Shinoda |
| 2016/0233714 A1* | 8/2016 | Lo ......................... H02J 7/0091 |
| 2017/0112196 A1* | 4/2017 | Sur ....................... H05B 1/0227 |
| 2017/0150758 A1 | 6/2017 | Fernando et al. |
| 2017/0207499 A1 | 7/2017 | Leadley |
| 2017/0250552 A1 | 8/2017 | Liu |
| 2019/0380394 A1 | 12/2019 | Takeuchi et al. |
| 2019/0386493 A1* | 12/2019 | Li ......................... H04R 1/1025 |
| 2019/0387806 A1* | 12/2019 | Nakano ................. H02J 7/0068 |

FOREIGN PATENT DOCUMENTS

| | | |
|---|---|---|
| JP | 2012-254016 A | 12/2012 |
| JP | 2014-027867 A | 2/2014 |
| JP | 2017-118696 A | 6/2017 |
| JP | 2018-085867 A | 5/2018 |
| JP | 2018-093877 A | 6/2018 |
| RU | 2 620 751 C2 | 5/2017 |
| WO | 2014-192834 A1 | 12/2014 |
| WO | 2015-165813 A1 | 11/2015 |
| WO | 2018-163262 A1 | 9/2018 |

OTHER PUBLICATIONS

European Search Report issued in related European Patent Application No. 20152149.9 dated May 15, 2020.
Notice of Reason for Refusal issued in related Japanese Patent Application No. 2019-035974 dated Jun. 18, 2019.
Search Report dated Jun. 3, 2022, in European Patent Application No. 22162438.0.
Office Action dated Apr. 11, 2022, in Eurasian Patent Application No. 202193036.

* cited by examiner

POWER SUPPLY UNIT FOR AEROSOL INHALER

CROSS-REFERENCE TO RELATED APPLICATIONS

This application is based upon and claims the benefit of priority from prior U.S. Provisional Application No. 62/793,551, filed on Jan. 17, 2019 and Japanese patent application No. 2019-035974, filed on Feb. 28, 2019, the entire contents of which are incorporated herein by reference.

TECHNICAL FIELD

The present invention relates to a power supply unit for an aerosol inhaler.

BACKGROUND ART

There is available an aerosol inhaler that includes an aerosol generation source, a load for generating an aerosol from the aerosol generation source, a power supply able to discharge power to the load, and a control unit controlling the power supply (for example, see Patent Literatures 1 to 3).

[Patent Literature 1] US 2017/0250552 A1
[Patent Literature 2] US 2015/0173124 A1
[Patent Literature 3] JP-A-2018-093877

Since an aerosol inhaler is frequently used, it is required to suppress deterioration of a power supply of the aerosol inhaler. As a charging device for charging a power supply, a device which controls charging outputs according to the temperature of a power supply is known. In such a charging device, for example, a method of supplying a normal charging voltage to a power supply, in a state where the temperature of the power supply is in a normal temperature range, and supplying a low charging voltage to the power supply in a state where the temperature of the power supply is high is performed.

However, in this method, the state where the normal charging voltage is supplied to the power supply may continue for a long time, and this becomes a cause of deterioration of the power supply.

In Patent Literatures 1 and 2, acquiring the temperature of a power supply is disclosed, however, any specific mode of charging control based on the acquired temperature is not disclosed. In Patent Literature 3, details of control on charging of a power supply are not disclosed.

An object of the present invention is to provide a power supply unit for an aerosol inhaler capable of suppressing deterioration of a power supply.

SUMMARY OF INVENTION

According to an aspect of the invention, there is provided a power supply unit for an aerosol inhaler, the power supply unit comprising: a power supply able to discharge power to a load for generating an aerosol from an aerosol generation source; and a charger including an information input part, and configured to be able to supply one of a first charging voltage and a second charging voltage lower than the first charging voltage to the power supply, based on an input value which is input from the information input part, wherein a fixed value which is predetermined as one input value can be input to the information input part, and the fixed value is a value for supplying the second charging voltage to the power supply.

DESCRIPTION OF EMBODIMENTS

Figure 1:
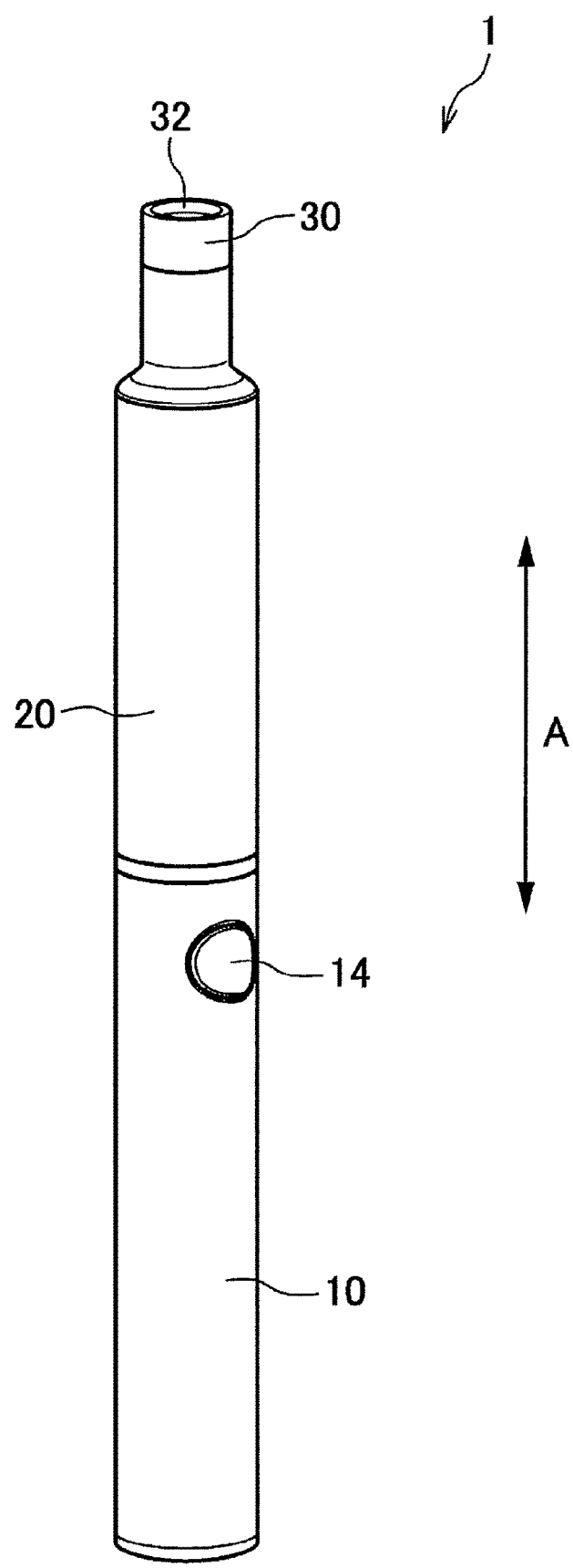
FIG. 1 is a perspective view of an aerosol inhaler equipped with a power supply unit of an embodiment of the present invention.
Figure 2:
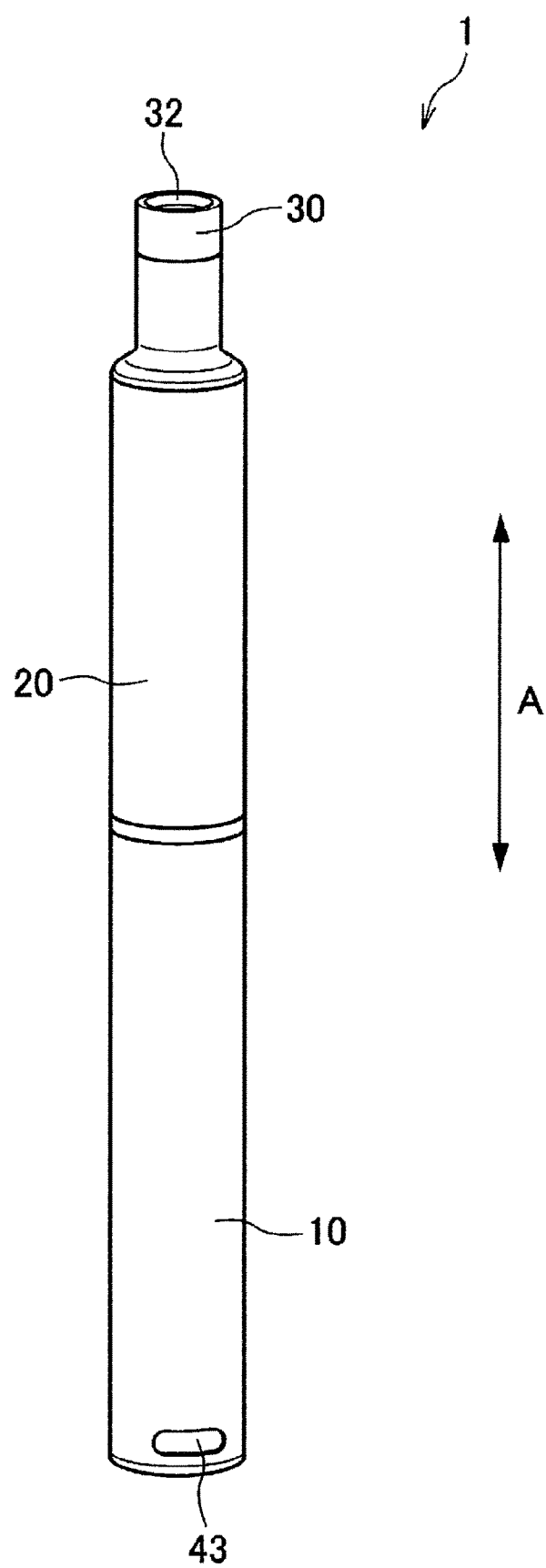
FIG. 2 is another perspective view of the aerosol inhaler of FIG. 1.

Hereinafter, a power supply unit for an aerosol inhaler according to an embodiment of the present invention will be described. First of all, an aerosol inhaler equipped with the power supply unit will be described with reference to FIG. 1 and FIG. 2.

(Aerosol Inhaler)

An aerosol inhaler 1 is a device for inhaling an aerosol containing a flavor without combustion, and has a rod shape extending along a certain direction (hereinafter, referred to as the longitudinal direction A). The aerosol inhaler 1 includes a power supply unit 10, a first cartridge 20, and a second cartridge 30 which are arranged in the order along the longitudinal direction A. The first cartridge 20 can be attached to and detached from the power supply unit 10. The second cartridge 30 can be attached to and detached from the first cartridge 20. In other words, the first cartridge 20 and the second cartridge 30 can be individually replaced.

(Power Supply Unit)

The power supply unit 10 of the present embodiment includes a power supply 12, a charging IC (Integrated Circuit) 55, an MCU (Micro Controller Unit) 50, a switch 19, a temperature sensor 17, various sensors, and so on inside a cylindrical power supply unit case 11, as shown in FIG. 3, FIG. 4, FIG. 5, and FIG. 6. As the MCU 50, an MCU whose shortest control cycle (the reciprocal of the maximum operation clock frequency) is longer than the shortest control cycle of the charging IC 55 is used.

The power supply 12 is a chargeable secondary battery, an electric double-layer capacitor, or the like, and is preferably a lithium-ion battery.

The temperature sensor 17 is configured, for example, with an temperature detection element whose resistance value changes according to temperature, specifically, an NTS (Negative Temperature Coefficient) thermistor. The temperature sensor 17 is for detecting the temperature of the power supply 12, and is disposed close to the power supply 12.

On a top part 11a of the power supply unit case 11 positioned on one end side in the longitudinal direction A (the first cartridge (20) side), a discharging terminal 41 is provided. The discharging terminal 41 is provided so as to protrude from the top surface of the top part 11a toward the first cartridge 20, and is configured to be able to be electrically connected to a load 21 of the first cartridge 20. Further, on a part of the top surface of the top part 11a in the vicinity of the discharging terminal 41, an air supply part 42 for supplying air to the load 21 of the first cartridge 20 is provided.

On a bottom part 11b of the power supply unit case 11 positioned on the other end side in the longitudinal direction A (the opposite side to the first cartridge 20), a charging terminal 43 able to be electrically connected to an external power supply is provided. The charging terminal 43 is provided on the side surface of the bottom part 11b, such that, for example, at least one of USB terminals, micro USB terminals, and lightning terminals (registered as a trade mark) can be connected thereto.

However, the charging terminal 43 may be a power receiving part able to receive power from an external power supply in a non-contact manner. In this case, the charging terminal 43 (the power receiving part) may be composed of a power receiving coil. The wireless power transfer system may be an electromagnetic induction type, or may be a magnetic resonance type. Also, the charging terminal 43 may be a power receiving part able to receive power from an external power supply without any contact point. As another example, the charging terminal 43 may be configured such that at least one of USB terminals, micro USB terminals, and lightning terminals can be connected thereto and the above-mentioned power receiving part is included therein.

On the side surface of the top part 11a of the power supply unit case 11, an operation unit 14 which the user can operate is provided so as to face the opposite side to the charging terminal 43. More specifically, the operation unit 14 and the charging terminal 43 are symmetric with respect to the point of intersection of a straight line connecting the operation unit 14 and the charging terminal 43 and the center line of the power supply unit 10 in the longitudinal direction A. The operation unit 14 is composed of a button type switch, a touch panel, or the like. In the vicinity of the operation unit 14, an inhalation sensor 15 for detecting puff actions are provided.

The charging IC 55 is disposed, for example, close to the charging terminal 43, and performs control to convert power which is input from an external power supply to the charging terminal 43 into charging power for the power supply 12 and supply the charging power to the power supply 12.

Figure 5:
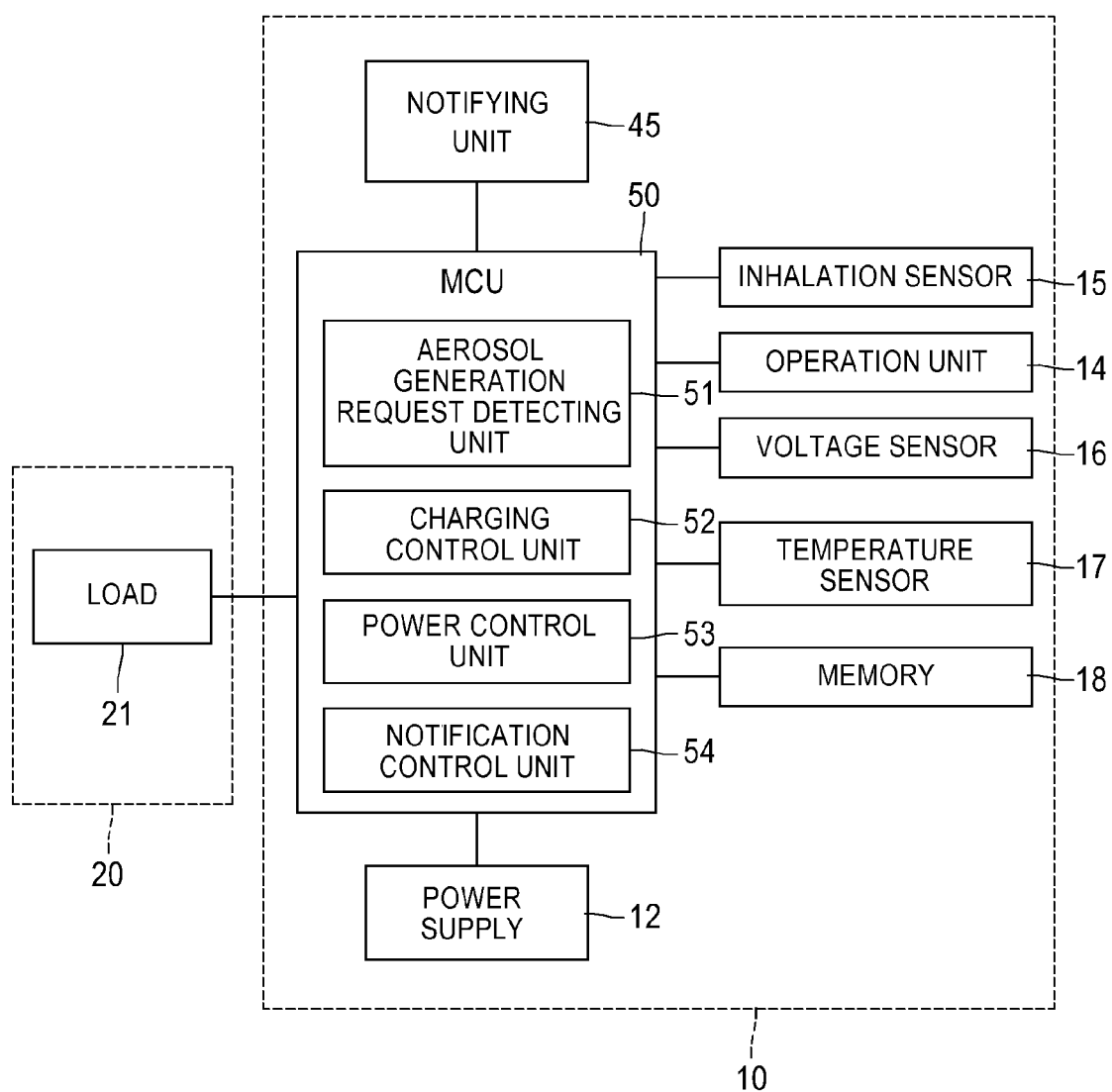
FIG. 5 is a block diagram illustrating the main part configuration of the power supply unit in the aerosol inhaler of FIG. 1.

The MCU 50 is connected to various sensor devices such as the inhalation sensor 15 for detecting puff (inhaling) actions, a voltage sensor 16 for measuring the power-supply voltage of the power supply 12, and a temperature sensor 17 provided to measure the temperature of the power supply 12, the operation unit 14, a notifying unit 45, and a memory 18 for storing the number of puff actions, the time for which power has been applied to the load 21, and so on, as shown in FIG. 5, and performs a variety of control on the aerosol inhaler 1. Specifically, the MCU 50 is mainly composed of a processor, and further includes storage media such as a RAM (Random Access Memory) necessary for the operation of the processor and a ROM (Read Only Memory) for storing a variety of information. In this specification, the processor is more specifically an electric circuit configured by combining circuit elements such as semiconductor elements.

Also, in the power supply unit case 11, an air intake (not shown in the drawings) for taking in air is formed. The air intake may be formed around the operation unit 14, or may be formed around the charging terminal 43.

(First Cartridge)

Figure 3:
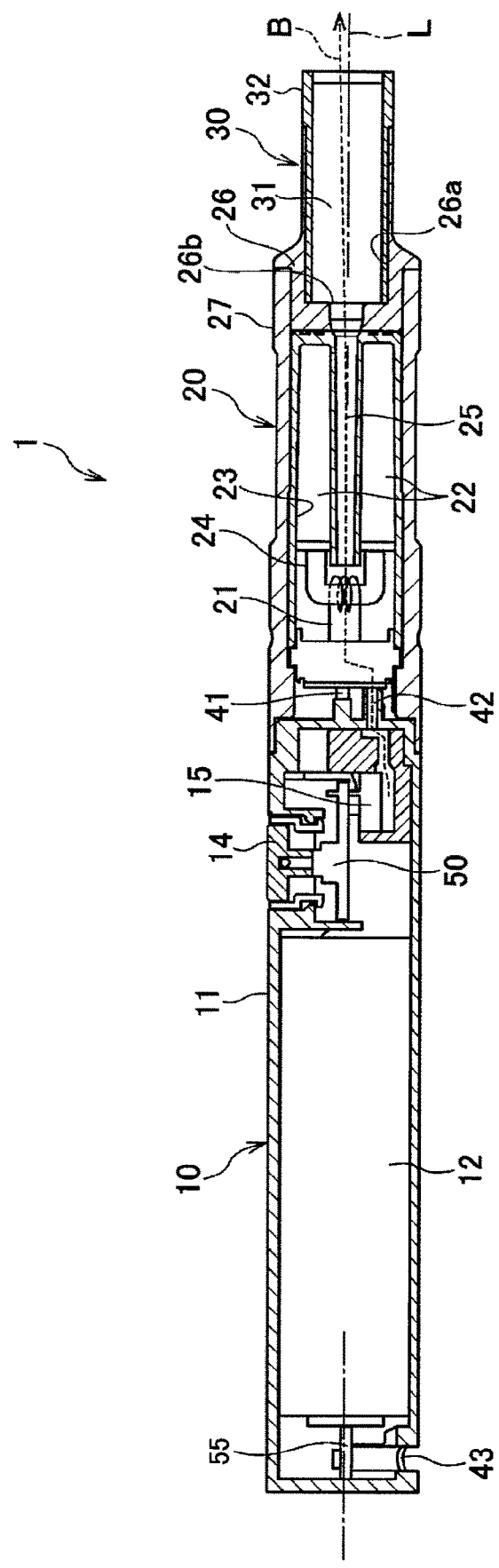
FIG. 3 is a cross-sectional view of the aerosol inhaler of FIG. 1.
Figure 4:
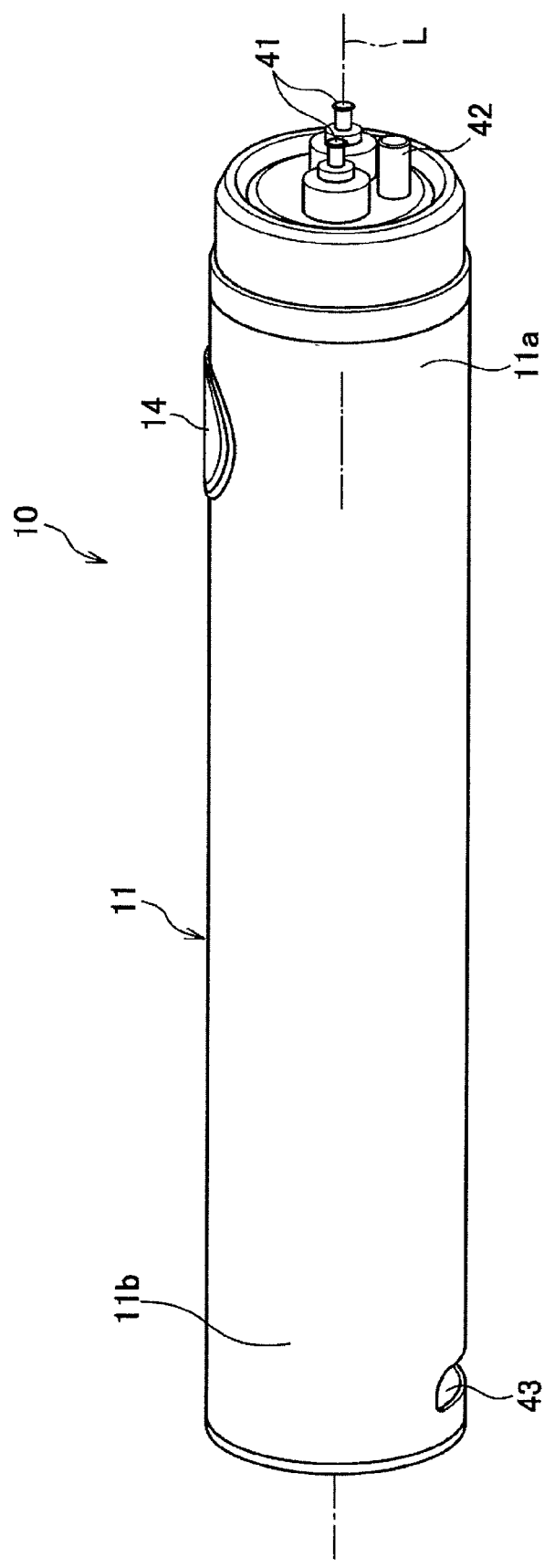
FIG. 4 is a perspective view of the power supply unit in the aerosol inhaler of FIG. 1.

As shown in FIG. 3, the first cartridge 20 includes a reservoir 23 for storing an aerosol source 22, the electric load 21 for atomizing the aerosol source 22, a wick 24 for drawing the aerosol source from the reservoir 23 toward the load 21, an aerosol channel 25 for an aerosol generated by atomizing the aerosol source 22 to flow toward the second cartridge 30, an end cap 26 for storing a part of the second cartridge 30, inside a cylindrical cartridge case 27.

The reservoir 23 is formed so as to surround the aerosol channel 25, and holds the aerosol source 22. In the reservoir 23, a porous member such as a resin web or cotton may be stored, and the porous member may be impregnated with the aerosol source 22. The aerosol source 22 includes a liquid such as glycerin, propylene glycol, or water.

The wick 24 is a liquid holding member for drawing the aerosol source 22 from the reservoir 23 toward the load 21 using capillarity, and is configured with, for example, glass fiber, a porous ceramic, or the like.

The load 21 atomizes the aerosol source 22, without combustion, by power which is supplied from the power supply 12 through the discharging terminal 41. The load 21 is configured with a heating wire wound with a predetermined pitch (a coil). However, the load 21 needs only to be an element capable of atomizing the aerosol source 22, thereby generating an aerosol, and is, for example, a heating element or an ultrasonic wave generator. Examples of the heating element include a heating resistor, a ceramic heater, an induction heating type heater, and so on.

The aerosol channel 25 is provided on the downstream side of the load 21 on the center line L of the power supply unit 10.

The end cap 26 includes a cartridge storage part 26a for storing a part of the second cartridge 30, and a connecting passage 26b for connecting the aerosol channel 25 and the cartridge storage part 26a.

(Second Cartridge)

The second cartridge 30 holds a flavor source 31. An end part of the second cartridge 30 on the first cartridge (20) side is stored in the cartridge storage part 26a provided in the end cap 26 of the first cartridge 20, so as to be able to be removed. Another end part of the second cartridge 30 on the opposite side to the first cartridge (20) side is configured as an inhalation port 32 for the user. However, the inhalation port 32 does not necessarily need to be configured integrally with the second cartridge 30 so as not to be separable from the second cartridge, and may be configured to be able to be attached to and detached from the second cartridge 30. If the inhalation port 32 is configured separately from the power supply unit 10 and the first cartridge 20 as described above, it is possible to keep the inhalation port 32 sanitary.

The second cartridge 30 adds a flavor to the aerosol generated by atomizing the aerosol source 22 by the load 21, by passing the aerosol through the flavor source 31. As a raw material piece which constitutes the flavor source, a compact made by forming shredded tobacco or a tobacco raw material into a grain shape can be used. The flavor source 31 may be configured with plants (such as mint, herbal medicines, herbs) other than tobacco. To the flavor source 31, a flavoring agent such as menthol may be added.

The aerosol inhaler 1 of the present embodiment can generate an aerosol containing the flavor by the aerosol source 22, the flavor source 31, and the load 21. In other words, the aerosol source 22 and the flavor source 31 constitute an aerosol generation source for generating an aerosol.

The aerosol generation source in the aerosol inhaler 1 is a part which the user can replace to use. For this part, for example, one first cartridge 20 and one or more (for example, five) second cartridges 30 can be provided as one set to the user.

The configuration of the aerosol generation source which can be used in the aerosol inhaler 1 is not limited to the configuration in which the aerosol source 22 and the flavor source 31 are configured separately, and may be a configuration in which the aerosol source 22 and the flavor source 31 are formed integrally, a configuration in which the flavor source 31 is omitted and the aerosol source 22 contains a substance which can be contained in the flavor source 31, a configuration in which the aerosol source 22 contains a medical substance or the like instead of the flavor source 31, or the like.

For an aerosol inhaler 1 including an aerosol generation source configured by integrally forming an aerosol source 22 and a flavor source 31, for example, one or more (for example, 20) aerosol generation sources may be provided as one set to the user.

In the case of an aerosol inhaler 1 including only an aerosol source 22 as an aerosol generation source, for example, one or more (for example, 20) aerosol generation sources may be provided as one set to the user.

In the aerosol inhaler 1 configured as described above, as shown by an arrow B in FIG. 3, air entering from the intake (not shown in the drawings) formed in the power supply unit case 11 passes through the air supply part 42, and passes near the load 21 of the first cartridge 20. The load 21 atomizes the aerosol source 22 drawn from the reservoir 23 by the wick 24. The aerosol generated by atomizing flows through the aerosol channel 25 together with the air entering from the intake, and is supplied to the second cartridge 30 through the connecting passage 26b. The aerosol supplied to the second cartridge 30 passes through the flavor source 31, whereby the flavor is added, and is supplied to the inhalation port 32.

Also, in the aerosol inhaler 1, the notifying unit 45 for notifying a variety of information is provided (see FIG. 5). The notifying unit 45 may be configured with a light emitting element, or may be configured with a vibrating element, or may be configured with a sound output element. The notifying unit 45 may be a combination of two or more elements of light emitting elements, vibrating elements, and sound output elements. The notifying unit 45 may be provided in any one of the power supply unit 10, the first cartridge 20, and the second cartridge 30; however, it is preferable that the notifying unit be provided in the power supply unit 10. For example, the area around the operation unit 14 is configured to have translucency to permit light which is emitted by light emitting elements such as LEDs to pass through.

(Electric Circuit)

Now, the details of the electric circuit of the power supply unit 10 will be described with reference to FIG. 6.

The power supply unit 10 includes, as main components, the power supply 12, the temperature sensor 17, the switch 19, a positive electrode side discharging terminal 41a and a negative electrode side discharging terminal 41b which constitute the discharging terminal 41, a positive electrode side charging terminal 43a and a negative electrode side charging terminal 43b which constitute the charging terminal 43, the MCU 50, the charging IC 55, resistors 61 and 62 composed of elements having resistance values, such as resistive elements or transistors, switches 63 and 64 composed of transistors such as MOSFETs, or the like, and a resistive element 65.

In the present embodiment, an example using "BQ24040DSQT" made by Texas Instruments Inc. as the charging IC 55 is shown; however, the charging IC is not limited thereto. The charging IC 55 has a plurality of pins including an IN pin (shown by "IN" in FIG. 6), an OUT pin (shown by "OUT" in FIG. 6), a TS pin (shown by "TS" in FIG. 6), a #CHG pin (shown by "#CHG" in FIG. 6), and an EP pin (shown by "EP" in FIG. 6), as pins for electrical connection with the outside. However, it should be noted that in the present embodiment, only main pins of pins which the charging IC 55 has are disclosed.

Also, in the present embodiment, an example using "PIC16F18346" made by Microchip Technology Inc. as the MCU 50 is shown; however, the MCU is not limited thereto. The MCU 50 has a plurality of pins including a Vdd pin (shown by "Vdd" in FIG. 6), an RA4 pin (shown by "RA4" in FIG. 6), a #RC3 pin (shown by "#RC3" in FIG. 6), a #RC4 pin (shown by "#RC4" in FIG. 6), a #RC5 pin (shown by "#RC5" in FIG. 6), a RB7 pin (shown by "RB7" in FIG. 6), and an EP pin (shown by "EP" in FIG. 6), as pins for electrical connection with the outside. However, it should be noted that in the present embodiment, only main pins of pins which the MCU 50 has are disclosed.

The IN pin of the charging IC 55 is an input terminal for power which is supplied from the charging terminal 43 (power for generating charging power). The IN pin of the charging IC 55 is connected to the positive electrode side charging terminal 43a.

The OUT pin of the charging IC 55 is an output terminal for the charging power generated by the charging IC 55. To the OUT pin of the charging IC 55, a power source line 60V is connected. This power source line 60V is connected to the positive electrode side discharging terminal 41a through the switch 19.

The EP pin of the charging IC 55 is a ground terminal. The EP pin of the charging IC 55 is connected to a ground line 60E which connects the negative electrode side charging terminal 43b and the negative electrode side discharging terminal 41b.

The #CHG pin of the charging IC 55 is a terminal for outputting charging state information indicating that charging is being performed, charging is stopped, or charging has been completed. The #CHG pin of the charging IC 55 is connected to the #RC5 pin of the MCU 50.

The TS pin of the charging IC 55 is a terminal for inputting a voltage value which is applied to a resistor which is connected thereto (a voltage value according to the resistance value of the corresponding resistor). From the voltage value input to the TS pin, the resistance value of the resistor which is connected to the TS pin (in other words, the temperature of the corresponding resistor) can be detected. When a thermistor is used as a resistor which is connected to the TS pin, it is possible to detect the temperature of the resistor which is connected to the TS pin, from a voltage value input to the TS pin.

The charging IC 55 has a function of controlling charging voltage to be output from the OUT pin, based on a voltage value which is input to the TS pin. Specifically, the charging IC 55 outputs a first charging voltage from the OUT pin, in the case where the temperature based on the voltage value which is input to the TS pin is lower than a threshold TH1, and outputs a second charging voltage lower than the first charging voltage, in the case where the temperature is equal to or higher than the threshold TH1 and is lower than a threshold TH2, and performs control to prevent charging voltage from being output from the OUT pin, i.e. to stop charging, in the case where the temperature is equal to or higher than the threshold TH2. The threshold TH1 is, for example, 45° C., and the threshold TH2 is, for example, 60° C.

The voltage value of the resistor which is connected to the TS pin in the case where the temperature of the resistor becomes the threshold TH1 is denoted by Vmax, and the voltage value of the resistor which is connected to the TS pin in the case where the temperature of the resistor becomes the threshold TH2 is denoted by Vmin. In the case where the resistor which is connected to the TS pin is an NTC thermistor, as the temperature of the resistor rises, the resistance value of the resistor decreases. Therefore, the relation of Vmax>Vmin is established. This should be noted. Based on the above-mentioned definition, the charging IC 55 outputs the second charging voltage from the OUT pin, in the case where the voltage value which is input to the TS pin is included in a predetermined range larger than Vmin and equal to or smaller than Vmax, and outputs the first charging voltage from the OUT pin, in the case where the voltage value which is input to the TS pin exceeds Vmax, and stops charging in the case where the voltage value which is input to the TS pin is smaller than Vmin.

To the TS pin of the charging IC 55 of the present embodiment, one end of the resistor 61 is connected. The other end of the resistor 61 is connected to the ground line 60E. Also, to the TS pin of the charging IC 55, one end of the switch 63 is connected. To the other end of the switch 63, one end of the resistor 62 is connected. The other end of the resistor 62 is connected to the ground line 60E.

Each of the resistor 61 and the resistor 62 has a predetermined fixed resistance value. The resistor 61, and the series circuit of the switch 63 and the resistor 62 are connected to the TS pin in parallel. Therefore, when the switch 63 is off (when it is nonconductive), a voltage value V1 on the resistor 61 which is caused by current flowing from the TS pin to the resistor 61 is input to the TS pin.

The voltage value V1 becomes a constant value since the resistance value of the resistor 61 is a fixed value. The resistance value of the resistor 61 is determined in advance such that the voltage value V1 becomes an arbitrary value in the above-mentioned performed range (larger than Vmin and equal to or smaller than Vmax). It is preferable to determine the resistance value of the resistor 61 in advance such that in the case where the median value of the predetermined range is Vc, the voltage value V1 becomes a value closer to Vmax than to Vc. In this case, even if the voltage value which is input to the TS pin changes due to noise or errors, it is possible to keep charging of the charging IC 55 on the power supply 12. As described above, the resistance value of the resistor 61 is determined such that the voltage value V1 becomes a value for outputting the second charging voltage from the OUT pin of the charging IC 55. The resistance value of the resistor 61 is specifically 4.7 kΩ.

Also, the resistance value of the resistor 62 is set to a value sufficiently smaller than the resistance value of the resistor 61. Therefore, when the switch 63 is on (when it is conductive), current preferentially flows from the TS pin to the resistor 62, and a voltage value V2 on the resistor 62 which is caused by the current is input to the TS pin.

This voltage value V2 becomes a constant value since the resistance value of the resistor 62 is a fixed value. The resistance value of the resistor 62 is determined in advance such that the voltage value V2 becomes an arbitrary value smaller than Vmin. As described above, the resistance value of the resistor 62 is determined in advance such that the voltage value V2 becomes a value for stopping charging of the charging IC 55 on the power supply 12.

However, the resistor 62 is not essential, and can be omitted. In other words, the other end of the switch 63 may be connected directly to the ground line 60E. In this case, when the switch 63 is on, the TS pin is grounded. Therefore, it is possible to make the voltage value to be input to the TS pin, smaller than Vmin. Therefore, by turning on the switch 63, it is possible to stop charging of the charging IC 55 on the power supply 12. Also, by omitting the resistor 62, it is possible to reduce the cost and the weight.

The positive electrode side of power supply 12 is connected to the power source line 60V, and the negative electrode side thereof is connected to the ground line 60E. Therefore, the power supply can be charged with the charging voltage output from the OUT pin of the charging IC 55 to the power source line 60V.

The Vdd pin of the MCU 50 is a power supply terminal, and is connected to the power source line 60V.

The EP pin of the MCU 50 is a ground terminal, and is connected to the ground line 60E.

The RA4 pin of the MCU 50 is connected to the switch 63, and is used as a terminal for performing control to turn on and off the switch 63.

The RB7 pin of the MCU 50 is connected to the switch 19, and is used as a terminal for performing control to turn on and off the switch 19.

The #RC5 pin of the MCU 50 is used as a terminal for receiving the charging state of the charging IC 55 from the #CHG pin of the charging IC 55.

The #RC4 pin of the MCU 50 is connected to the switch 64, and is used as a terminal for performing control to turn on and off the switch 64. One end of the switch 64 is connected to the power source line 60V, and the other end thereof is connected to one end of the resistive element 65. The other end of the resistive element 65 is connected to one end of the NTC thermistor constituting the temperature sensor 17. The other end of the NTC thermistor constituting the temperature sensor 17 is connected to the ground line 60E.

The #RC3 pin of the MCU 50 is used as a terminal for detecting the temperature of the power supply 12. The #RC3 pin of the MCU 50 is connected to the connection point between the resistive element 65 and the temperature sensor 17.

When the switch 64 is on (when it is conductive), the voltage on the power source line 60V is divided by the resistive element 65 and the temperature sensor 17, and the voltage value which is applied to the temperature sensor 17 is input to the #RC3 pin of the MCU 50. The MCU 50 has a function of acquiring the temperature of the power supply 12 based on the voltage value which is input to the #RC3 pin, as will be described below.

Meanwhile, when the switch 64 is off (when it is nonconductive), voltage is not supplied to the temperature sensor 17. Therefore, in this case, the MCU 50 changes to the state where it cannot acquire the temperature of the power supply 12.

The switch 19 is composed of, for example, a semiconductor element such as a MOSFET, and is turned on and off under the control of the MCU 50.

Figure 6:
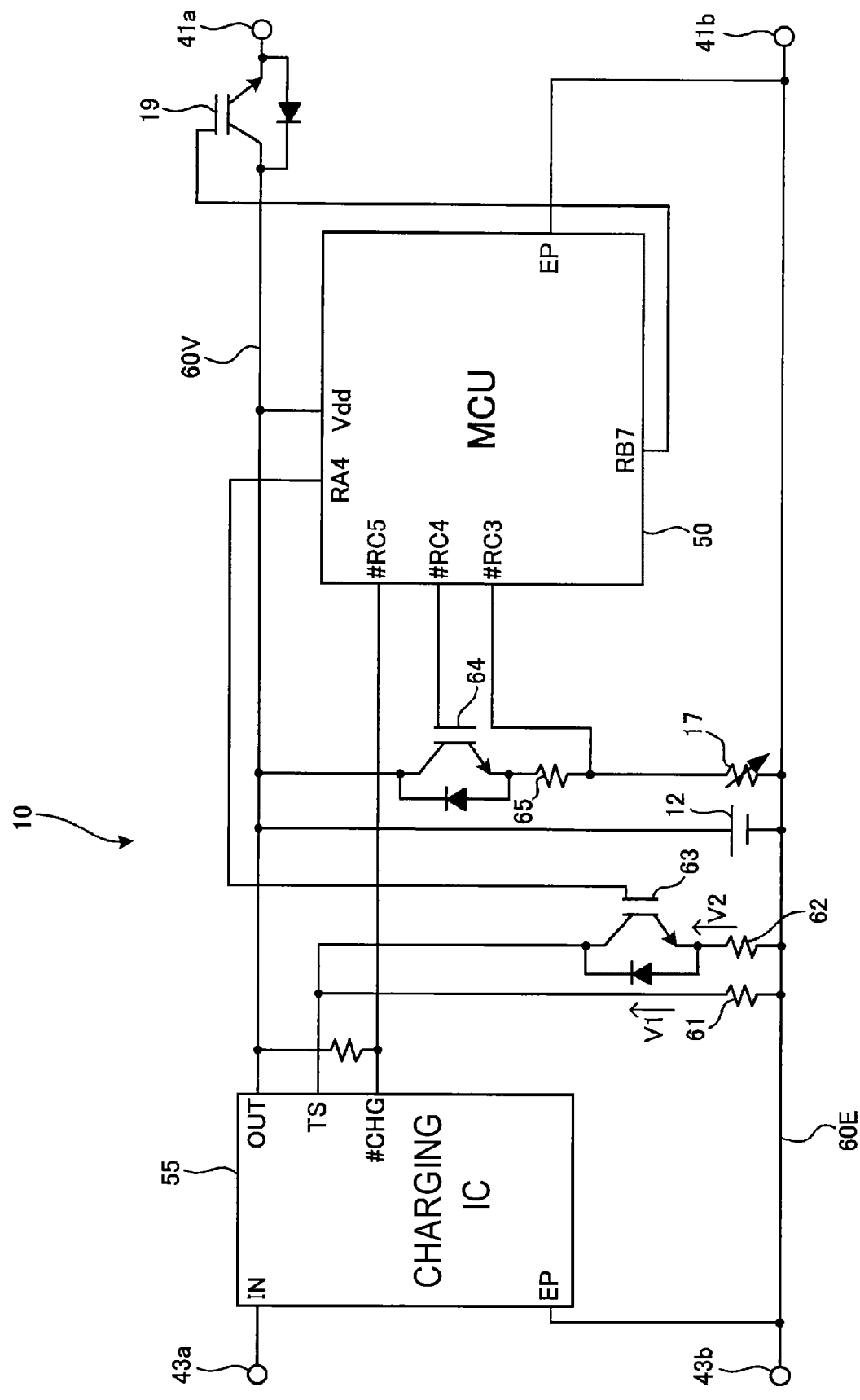
FIG. 6 is a schematic diagram illustrating the main part circuit configuration of the power supply unit in the aerosol inhaler of FIG. 1.

In the electric circuit of the power supply unit 10 shown in FIG. 6, the switch 19 is provided between the positive electrode side of the power supply 12 and the positive electrode side discharging terminal 41a. Instead of this so-called plus control type, the switch 19 may be a minus control type which is provided between the negative electrode side discharging terminal 41b and the negative electrode side of the power supply 12.

(MCU)

Now, the configuration of the MCU 50 will be described in more detail.

As shown in FIG. 5, the MCU 50 includes an aerosol generation request detecting unit 51, a charging control unit 52, a power control unit 53, and a notification control unit 54, as functional blocks which are realized by executing a program stored in the ROM by a processor.

The aerosol generation request detecting unit 51 detects a request for aerosol generation based on the output result of the inhalation sensor 15. The inhalation sensor 15 is configured to output the value of a variation in the pressure in the power supply unit 10 (the internal pressure) caused by inhalation of the user through the inhalation port 32. The inhalation sensor 15 is, for example, a pressure sensor for outputting an output value (for example, a voltage value or a current value) according to the internal pressure which varies according to the flow rate of air which is sucked from the intake (not shown in the drawings) toward the inhalation port 32 (i.e. a puff action of the user). The inhalation sensor 15 may be configured with a capacitor microphone or the like.

The power control unit 53 controls discharging of the power supply 12 through the discharging terminal 41 by switching on and off the switch 19, if the aerosol generation request detecting unit 51 detects the request for aerosol generation.

The power control unit 53 performs control such that the amount of aerosol which is generated by atomizing the aerosol source by the load 21 falls in a desired range, i.e. such that power or the amount of power which is supplied from the power supply 12 to the load 21 falls in a predetermined range. Specifically, the power control unit 53 controls switching on and off of the switch 19 by, for example, PWM (Pulse Width Modulation) control. Alternatively, the power control unit 53 may control switching on and off of the switch 19 by PFM (Pulse Frequency Modulation) control.

After supply of power to the load 21 starts in order to generate an aerosol, if a predetermined period passes, the power control unit 53 stops supply of power from the power supply 12 to the load 21. In other words, even while the user is actually performing a puff action, if the puff period exceeds a certain period, the power control unit 53 stops supply of power from the power supply 12 to the load 21. The certain period is determined to suppress variation in user's puff period.

By control of the power control unit 53, the current which flows in the load 21 during one puff action becomes substantially a constant value which is determined according to substantially constant effective voltage which is supplied to the load 21 by PWM control, and the resistance values of the discharging terminal 41 and the load 21. In the aerosol inhaler 1 of the present embodiment, when the user inhales an aerosol using one unused second cartridge 30, the cumulative time for which power can be supplied to the load 21 is controlled to a maximum of, for example, 120 seconds. To this end, it is possible to obtain the maximum amount of power required to empty (use up) one second cartridge 30 in advance.

The notification control unit 54 controls the notifying unit 45 such that the notifying unit notifies a variety of information. For example, the notification control unit 54 controls the notifying unit 45 in response to detection of the timing to replace the second cartridge 30, such that the notifying unit notifies the timing to replace the second cartridge 30. The notification control unit 54 detects and notifies the timing to replace the second cartridge 30, based on the cumulative number of puff actions or the cumulative time for which power has been supplied to the load 21, stored in the memory 18. The notification control unit 54 is not limited to notification of the timing to replace the second cartridge 30, and may notify the timing to replace the first cartridge 20, the timing to replace the power supply 12, the timing to charge the power supply 12, and so on.

In the state where one unused second cartridge 30 is set, if a predetermined number of puff actions are performed, or if the cumulative time for which power has been applied to the load 21 due to puff actions reaches a predetermined value (for example, 120 seconds), the notification control unit 54 determines that the second cartridge 30 is used up (i.e. the remaining amount is zero or the second cartridge is empty), and notifies the timing to replace the second cartridge 30.

Also, in the case of determining that all of the second cartridges 30 included in one set are used up, the notification control unit 54 may determine that one first cartridge 20 included in the single set is used up (i.e. the remaining amount is zero or the first cartridge is empty), and notify the timing to replace the first cartridge 20.

The charging control unit 52 acquires the temperature of the power supply 12 based on a voltage value which is input to the #RC3 pin, and controls switching on and off of the switch 63, thereby controlling the charging voltage to be supplied to the power supply 12.

(Power Supply Charging Operation)

The operation of the aerosol inhaler 1 having the above-described configuration during charging of the power supply 12 will be described.

If a charging cable is connected to the charging terminal 43, and this charging cable is connected to an external power supply, a charging start signal is input from the #CHG pin of the charging IC 55 to the #RC5 pin of the MCU 50. Also, in a state before the charging start signal is input to the #RC5 pin of the MCU 50, the switch 63 and the switch 64 are off. In other words, if charging is started, the voltage value V1 according to the resistance value of the resistor 61 is input to the TS pin of the charging IC 55, and the power supply 12 is charged with the second charging voltage.

After the charging start signal is input to the #RC5 pin of the MCU 50, the MCU 50 regularly acquires the temperature of the power supply 12. Specifically, the MCU 50 performs acquisition of the temperature of the power supply 12 in a cycle longer than the shortest control cycle of the MCU 50 (i.e. at a frequency lower than the maximum operation frequency of the power supply unit, in other words, at an operation clock frequency lower than the maximum operation clock frequency). When a timing to acquire the temperature of the power supply 12 comes, the MCU 50 turns on the switch 64, and acquires the temperature Tbatt of the power supply 12 based on the voltage value which is input to the #RC3 pin, and turns off the switch 64.

Then, the MCU 50 determines whether the acquired temperature Tbatt is equal to or higher than the above-mentioned threshold TH2, or not, and if the temperature Tbatt is lower than the threshold TH2, the MCU waits for the next temperature acquisition timing. Meanwhile, if the temperature Tbatt is equal to or higher than the threshold TH2, the MCU 50 performs control to turn on the switch 63. According to this control, the voltage value V2 according to the resistance value of the resistor 62 is input to the TS pin of the charging IC 55. Then, the charging IC 55 stops supply of the charging voltage to the power supply 12. If charging of the power supply 12 is stopped, a charging stop signal is output from the #CHG pin of the charging IC 55, and the MCU 50 receives this signal and returns the switch 63 to the OFF state.

As described above, according to the power supply unit 10 of FIG. 6, the charging IC 55 charges the power supply 12 with the second charging voltage lower than the first charging voltage which is the highest charging voltage which the charging IC can output. In this case, it becomes possible to continuously charge the power supply 12 with a low charging voltage. Therefore, charging and discharging of the power supply 12 can be repeated in a state lower than a fully charged state, whereby it becomes possible to suppress deterioration of the power supply 12.

Also, the power supply 12 needs only to have such capacity that it is possible to supply such an amount of power that it is possible to empty one set of unused aerosol generation sources, to the load 21, if charging of the power supply in a brand new state (a state where a numerical index indicating the state of deterioration of the power supply 12 is smaller than a threshold) with the second charging voltage is completed. In this case, even in the case of performing charging with a low charging voltage, if the power supply 12 is in the fully charged state, it can empty one set of unused aerosol generation sources. Therefore, it is possible to improve convenience for users while suppressing deterioration of the power supply.

Also, the power supply 12 needs only to be configured to have such capacity that even though deterioration progresses (the numerical index indicating the state of deterioration of the power supply 12 becomes equal to or smaller than the threshold), if charging with the second charging voltage is completed, it is possible to supply an amount of power capable of emptying one set of unused aerosol generation sources to the load 21. According to this configuration, even if deterioration of the power supply 12 progresses, if the power supply 12 is in the fully charged state, it can empty one set of unused aerosol generation sources. Therefore, it is possible to improve convenience for users while suppressing deterioration of the power supply.

As the numerical index indicating the state of deterioration of the power supply 12, for example, the rate of increase in the internal resistance of the power supply 12, the cumulative amount of power charged and discharged, the state of heath (SOH), and the like may be used. By the way, in the case of using the SOH, it is preferable to perform such formula manipulation that the numeric value increases as deterioration of the power supply 12 progresses.

Also, according to the power supply unit 10, even in the case of using a charging IC 55 which needs a variable resistor to be connected to the TS pin when it is used, control to charge the power supply 12 with only a low charging voltage becomes possible. Therefore, it is not necessary to newly design a charging IC for generating a low charging voltage, and it is possible to reduce the manufacturing cost of the power supply unit 10.

By the way, in the power supply unit 10, since the resistance value of the resistor which is connected to the TS pin of the charging IC 55 is fixed, it is not possible to detect the temperature of the power supply 12 by the charging IC 55. However, the MCU 50 acquires the temperature of the power supply 12, and performs protection of the power supply 12 based on the acquired temperature. Therefore, it is possible to prevent deterioration of the power supply 12 from being caused by a rise in the temperature.

Also, the MCU 50 acquires the temperature of the power supply 12 in a cycle longer than the shortest control cycle of the MCU 50. Therefore, the temperature of the power supply 12 is not acquired at an excessive frequency, so it is possible to reduce the power consumption. Also, it is possible to use calculation resources of the MCU 50 for other purposes.

Also, the MCU 50 can perform switching between a state where it is possible to acquire the temperature of the power supply 12 and a state where it is impossible to acquire the temperature of the power supply 12, by controlling switching on and off of the switch 64. Since acquisition of the temperature becomes possible by easy control using the switch 64 as described above, it is possible to suppress the manufacturing cost. Also, since the temperature of the power supply 12 can be acquired only at timings when it is required, it is possible to reduce the power consumption.

Figure 7:
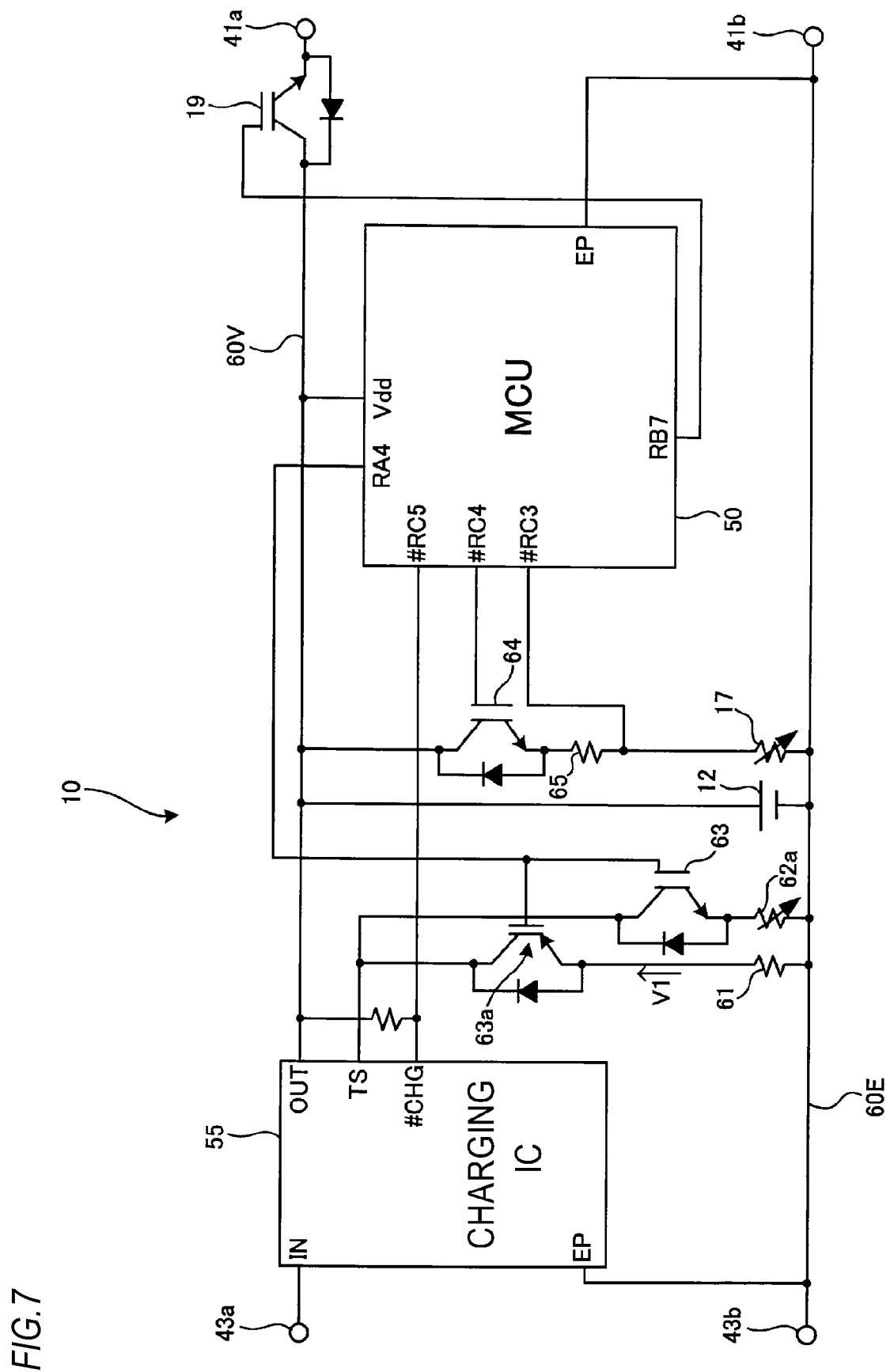
FIG. 7 is a schematic diagram illustrating a modification of the main part circuit configuration of the power supply unit in the aerosol inhaler of FIG. 1.

FIG. 7 is a view illustrating a modification of the power supply unit 10 shown in FIG. 6. A power supply unit 10 shown in FIG. 7 has the same configuration as that of FIG. 6 except that it has an NTC thermistor 62a in place of the resistor 62 and further includes a switch 63a between the resistor 61 and the TS pin.

The NTC thermistor 62a is disposed close to the power supply 12, and a thermistor identical to the temperature sensor 17 can be used.

The switch 63a is turned on and off by control using a signal which is outputted from the RA4 pin of the MCU 50 or any other pin (not shown in the drawing).

In an aerosol inhaler 1 which is equipped with the power supply unit 10 shown in FIG. 7, it is possible to set a first charging mode for maintaining the charging voltage for the power supply 12 at the second charging voltage, and a second charging mode for making it possible to switching the charging voltage for the power supply 12 between the first charging voltage and the second charging voltage. Switching between the first charging mode and the second charging mode can be performed by a user's operation on the operation unit 14. Hereinafter, the charging operation of the power supply unit 10 of FIG. 7 during the first charging mode and the charging operation of the power supply unit during the second charging mode will be described.

(Charging Operation During First Charging Mode)

If the temperature of the power supply 12 is lower than the threshold TH2, the MCU 50 performs control to turn on the switch 63a, and performs control to turn off the switch 63. Meanwhile, if the temperature of the power supply 12 is equal to or higher than the threshold TH2, the MCU 50 performs control to turn off the switch 63a, and performs control to turn on the switch 63. In the case where the temperature of the power supply 12 is equal to or higher than the threshold TH2, the resistance value of the NTC thermistor 62a becomes a small value according to the temperature equal to or higher than the threshold TH2. Therefore, to the TS pin, a voltage value equal to or smaller than Vmin is input, and the charging IC 55 is stopped from charging.

(Charging Operation During Second Charging Mode)

Always, the MCU 50 performs control to maintain the switch 63a and performs control to maintain the switch 63 in the ON state. Also, the MCU 50 does not perform the process of acquiring the temperature of the power supply 12. If the switch 63a is turned off and the switch 63 is turned on, to the TS pin, the value of voltage varying according to the temperature of the power supply 12 is input. Therefore, the charging IC 55 outputs the first charging voltage from the OUT pin, in the case where the temperature based on the voltage value input to the TS pin is lower than the threshold TH1, and outputs the second charging voltage from the OUT pin, in the case where the temperature is equal to or higher than the threshold TH1 and is lower than the threshold TH2, and performs control to stop charging, in the case where the temperature is equal to or higher than the threshold TH2.

As described above, according to the power supply unit 10 of FIG. 7, it becomes possible to perform switching between the second charging mode for performing switching between the first charging voltage and the second charging voltage based on the temperature of the power supply 12 and the first charging mode for performing charging with only the second charging voltage based on the fixed value, and flexible charging control becomes possible. Also, in any of the charging modes, in the case where the temperature of the power supply 12 is equal to or higher than the threshold TH2, it is possible to stop charging of the power supply 12, so protection of the power supply 12 becomes possible.

In the electric circuits of FIG. 6 and FIG. 7 described above, the ground line 60E is a grounded wiring line; however, it needs only to be a wiring line having the lowest potential (a main negative bus line) in the power supply unit 10, and may not be a grounded wiring line.

In this specification, at least the following inventions (1) to (15) are disclosed. Moreover, although the corresponding constituent elements and the like in the embodiments described above are shown in parentheses, it is not limited thereto.

(1) A power supply unit for an aerosol inhaler, the power supply unit comprising:
 a power supply (the power supply 12) able to discharge power to a load for generating an aerosol from an aerosol generation source; and
 a charger (the charging IC 55) including an information input part (the TS pin), and configured to be able to supply one of a first charging voltage and a second charging voltage lower than the first charging voltage to the power supply, based on an input value which is input from the information input part,
 wherein a fixed value (the voltage value V1) which is predetermined as one input value can be input to the information input part, and
 the fixed value is a value for supplying the second charging voltage to the power supply.

According to (1), in a state where the fixed value is being input to the information input part, it is possible to charge the power supply with the second charging voltage lower than the first charging voltage. For example, by realizing a state where the fixed value is continuously input to the information input part, it becomes possible to continuously charge the power supply with a low charging voltage, and it becomes possible to suppress deterioration of the power supply.

(2) The power supply unit according to (1), wherein
 the input values is a value related to voltage to be applied to a resistor which is connected to the information input part,
 the power supply unit includes a fixed resistor (the resistor 61) having a fixed resistance value and connected to the information input part, and
 a value related to voltage to be applied to the fixed resistor can be input as the fixed value to the information input part.

For example, as long as the charger is configured to be able to supply the first charging voltage to the power supply in the case where the temperature of the power supply is low, and supply the second charging voltage to the power supply in the case where the temperature of the power supply is high, as disclosed in (2), if a value corresponding to the case where the temperature of the power supply is high is set as the fixed resistance value of the resistor, it becomes possible to input a value for supplying the second charging voltage to the power supply, to the information input part.

(3) The power supply unit according to (2), wherein
 the charger supplies the second charging voltage in a case where an input value which is input from the information input part is included in a predetermined range (the range larger than Vmin and equal to or smaller than Vmax), and
 the resistance value of the fixed resistor is a value closer to a second value for making the fixed value into a maximum value (Vmax) in the predetermined range, than to a first value for making the fixed value into a minimum value (Vmin) in the predetermined range.

For example, in the case where the charger performs control to reduce the second charging voltage as the input value decreases in a defined range, according to the configuration of (3), it is possible to increase the second charging voltage. Therefore, it is possible to make high-speed charging possible while suppressing deterioration of the power supply. Also, even if the input voltage changes due to noise or an error, it is possible to keep charging of the charger on the power supply.

(4) The power supply unit according to (2), wherein
 the resistance value of the fixed resistor is 4.7 kΩ.

According to (4), for example, in the case of using BQ24040DSQT made by Texas Instruments Inc. as the charger, it is possible to make the fixed value into a value for supplying the second charging voltage to the power supply.

(5) The power supply unit according to any one of (1) to (4), further comprising:
 a control device (the MCU 50) separate from the charger, wherein the control device is configured to be able to acquire temperature of the power supply.

According to (5), since the control device can acquire the temperature of the power supply, it is possible to perform control on charging and discharging of the power supply, protection of the power supply, and so on, based on the temperature of the power supply.

(6) The power supply unit according to (5), wherein
 the control device acquires the temperature of the power supply, in a cycle longer than a shortest control cycle of the control device, or at a frequency lower than a maximum operation frequency of the control device.

According to (6), since the temperature of the power supply is not acquired at an excessive frequency, it is possible to reduce the power consumption. Also, it is possible to use calculation resources of the control device for other purposes.

(7) The power supply unit according to (5), wherein
 the control device performs control on switching between a state where the temperature of the power supply can be acquired and a state where the temperature of the power supply cannot be acquired.

According to (7), since the temperature of the power supply can be acquired at timings when the temperature is required, it is possible to reduce the power consumption. Also, it is possible to use calculation resources of the control device for other purposes. Further, it is possible to improve the accuracy of control using the temperature of the power supply.

(8) The power supply unit according to any one of (1) to (7), further comprising:
 a switch (the switch 63) able to perform switching between the state where the fixed value is input to the information input part and a state where the fixed value is not input to the information input part, According to (8), since it is possible to input input values other than the fixed value to the information input part, it becomes possible to change the operation mode of the charger if needed.

(9) The power supply unit according to (8), wherein
in the state where the fixed value is not input to the information input part, the switch causes the charger to input a value (the voltage value V2) for stopping charging of the power supply, to the information input part.

According to (9), in a state where the fixed value is not input to the information input part, it is possible to stop the charger from charging the power supply. For example, in the case where the temperature of the power supply is such high that protection of the power supply is required, by inputting the value for stopping charging of the power supply to the information input part, it is possible to protect the power supply.

(10) The power supply unit according to (8), wherein
the input value is a value related to voltage to be applied to a resistor which is connected to the information input part,
the power supply unit includes a fixed resistor having a fixed resistance value and connected to the information input part,
the switch is provided between the information input part and a main negative bus line or a ground line (the ground line 60E), and
the information input part and the main negative bus line or the ground line are directly connected by the switch, whereby the fixed value is not input to the information input part.

According to (10), since the information input part and either the main negative bus line or the ground line are directly connected, it is possible to make the value related to voltage to be input to the information input part, into a sufficiently small value. In the case of using, as the charger, one having a function of stopping charging if the value which is input to the information input part becomes smaller than a threshold (Vmin), in the corresponding state, it is possible to stop the charger from charging, so it is possible to protect the power supply.

(11) The power supply unit according to (8), further comprising:
an element (the NTC thermistor 62a) whose physical property value changes based on temperature of the power supply,
wherein, in the state where the fixed value is not input to the information input part, the switch connects the element to the information input part.

According to (11), it becomes possible to perform switching between a mode for performing switching between the first charging voltage and the second charging voltage based on the temperature of the power supply and a mode for performing charging with the second charging voltage based on the fixed value, and flexible charging control becomes possible.

(12) The power supply unit according to any one of (1) to (11), wherein
the power supply, which is brand new, in a case where charging of the power supply with the second charging voltage is completed, has such capacity that the power supply can supply to the load such an amount of power as to empty the aerosol generation source, which is unused.

According to (12), even in the case where the power supply is brand new, if charging with a low charging voltage is completed, it is possible to empty the aerosol generation source. Therefore, it is possible to improve convenience for users while suppressing deterioration of the power supply.

(13) The power supply unit according to (12), wherein
the power supply, in which a numerical index indicating a state of deterioration of the power supply is equal to or larger than a threshold, in the case where the charging of the power supply with the second charging voltage is completed, has such capacity that the power supply can supply to the load such an amount of power as to empty the aerosol generation source, which is unused.

According to (13), even in the case where deterioration of the power supply has progressed, if charging with a low charging voltage is completed, it is possible to empty the aerosol generation source. Therefore, it is possible to improve convenience for users while suppressing deterioration of the power supply.

(14) A power supply unit for an aerosol inhaler, the power supply unit comprising:
a power supply (the power supply 12) able to discharge power to a load for generating an aerosol from an aerosol generation source;
a first control device (the charging IC 55); and
a second control device separate from the first control device and having a control cycle shorter than that of the first control device,
wherein, of the first control device and the second control device, only the second control device is configured to be able to acquire temperature of the power supply.

According to (14), it is possible to acquire the temperature of the power supply by the second control device having a short control cycle, i.e. having high processing performance. Therefore, it is possible to accurately acquire the temperature at high frequency, and it becomes possible to perform high-accurate control on charging and discharging, protection of the power supply, and so on, based on the temperature. As a result, it is possible to suppress deterioration of the power supply.

(15) The power supply unit according to (14), wherein
the first control device is a charger configured to convert power which is input, into charging power for the power supply, and
the second control device is a device configured to perform control on discharging and charging of the power supply.

According to (15), since it is possible to acquire the temperature of the power supply by the device configured to control discharging of the power supply, it is possible to perform high-accuracy charging control using the acquired temperature by the second control device, and it becomes possible to perform high-accuracy charging control while suppressing the cost of the first control device.

What is claimed is:

1. A power supply unit for an aerosol inhaler, the power supply unit comprising:
a power supply able to discharge power to a load for generating an aerosol from an aerosol generation source;
a temperature sensor that detects temperature of the power supply; and
a charger configured to convert power, which is supplied from an external power supply, into charging power for the power supply,
wherein the charger includes an information input part, and is configured to be able to supply one of a first charging voltage and a second charging voltage lower than the first charging voltage to the power supply, based on an input value which is input from the information input part,
a fixed value which is predetermined as one input value can be input to the information input part,
the fixed value is a value for supplying the second charging voltage to the power supply, and
the fixed value is constantly input to the information input part regardless of the temperature of the power supply from a beginning to an end of charging when the power supply is being charged.

2. The power supply unit according to claim 1, wherein
the input value relates to voltage to be applied to a fixed resistor which is connected to the information input part,
the power supply unit includes the fixed resistor having a fixed resistance value and connected to the information input part, and
the fixed value relates to voltage to be applied to the fixed resistor.

3. The power supply unit according to claim 2, wherein
the charger supplies the second charging voltage in a case where the input value which is input from the information input part is included in a predetermined range, and
the fixed resistance value of the fixed resistor is a value closer to a second value for making the fixed value into a maximum value in the predetermined range, than to a first value for making the fixed value into a minimum value in the predetermined range.

4. The power supply unit according to claim 2, wherein
the fixed resistance value of the fixed resistor is 4.7 kΩ.

5. The power supply unit according to claim 1, further comprising:
a control device separate from the charger,
wherein the control device is configured to be able to acquire temperature of the power supply.

6. The power supply unit according to claim 5, wherein
the control device acquires the temperature of the power supply, in a cycle longer than a shortest control cycle of the control device, or at a frequency lower than a maximum operation frequency of the control device.

7. The power supply unit according to claim 5, wherein
the control device performs control on switching between a state where the temperature of the power supply can be acquired and a state where the temperature of the power supply cannot be acquired.

8. The power supply unit according to claim 1, further comprising:

a switch able to perform switching between a state where the fixed value is input to the information input part and a state where the fixed value is not input to the information input part.

9. The power supply unit according to claim 8, wherein
in the state where the fixed value is not input to the information input part, the switch causes the charger to input a value for stopping charging of the power supply, to the information input part.

10. The power supply unit according to claim 8, wherein
the input value is a value related to voltage to be applied to a resistor which is connected to the information input part,
the power supply unit includes a fixed resistor having a fixed resistance value and connected to the information input part,
the switch is provided between the information input part and a main negative bus line or a ground line, and
the information input part is connected to one end of the switch and the main negative bus line or the ground line is connected to the other end of the switch, whereby the fixed value is not input to the information input part.

11. The power supply unit according to claim 8, further comprising:
a temperature detection element whose physical property value changes based on temperature of the power supply,
wherein, in the state where the fixed value is not input to the information input part, the switch connects the element to the information input part.

12. The power supply unit according to claim 1, wherein
in a case where the power supply has never been used and charging of the power supply with the second charging voltage is completed, the power supply has capacity by which the load is able to supply power to use up the aerosol generation source which has never been used.

13. The power supply unit according to claim 12, wherein
in a case where a numerical index indicating a state of deterioration of the power supply is equal to or larger than a threshold and the charging of the power supply with the second charging voltage is completed, the power supply has such capacity by which the load is able to supply power to use up the aerosol generation source which has never been used.

14. The power supply unit according to claim 1,
wherein the fixed value is unaffected by a temperature of the power supply.

15. The power supply unit according to claim 1, the power supply unit comprising:
a control device separate from the power supply and having an operation clock frequency higher than an operation clock frequency of the power supply,
wherein, of the power supply and the control device, only the control device is configured to be able to acquire temperature of the power supply.

16. The power supply unit according to claim 1, wherein
when the temperature of the power supply is lower than a threshold, the charger supplies the second charging voltage based on the fixed value constantly input to the information input part from the beginning of charging, and
when the temperature of the power supply is equal to or higher than the threshold, the charger stops supply of any charging voltage.

* * * * *